(12) United States Patent
Melamed

(10) Patent No.: US 11,083,389 B2
(45) Date of Patent: *Aug. 10, 2021

(54) SENSORS FOR A PORTABLE DEVICE

(71) Applicant: VAYYAR IMAGING LTD, Yehud (IL)

(72) Inventor: Raviv Melamed, Nes Ziona (IL)

(73) Assignee: VAYYAR IMAGING LTD, Yehud (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/793,745

(22) Filed: Feb. 18, 2020

(65) Prior Publication Data
US 2020/0178838 A1 Jun. 11, 2020

Related U.S. Application Data

(63) Continuation of application No. 16/426,577, filed on May 30, 2019, now abandoned, which is a
(Continued)

(51) Int. Cl.
*A61B 5/0507* (2021.01)
*G01S 7/02* (2006.01)
(Continued)

(52) U.S. Cl.
CPC ............ *A61B 5/0507* (2013.01); *A61B 5/004* (2013.01); *A61B 5/0033* (2013.01);
(Continued)

(58) Field of Classification Search
CPC ..... A61B 5/0507; A61B 5/0033; A61B 5/004; A61B 5/4312; A61B 5/4872;
(Continued)

(56) References Cited

U.S. PATENT DOCUMENTS 5,188,221 A 2/1993 Bertrand
7,099,496 B2 8/2006 Benkley, III
(Continued)

OTHER PUBLICATIONS

Supplementary European Search Report for corresponding EP15742707.1 dated Aug. 31, 2017.
(Continued)

*Primary Examiner* — Melissa J Koval
*Assistant Examiner* — Trung Q Nguyen
(74) *Attorney, Agent, or Firm* — Browdy and Neimark, PLLC

(57) ABSTRACT

A portable sensing system device and method for providing microwave or RF (radio-frequency) sensing functionality for a portable device, the device comprising: a portable device housing configured to be carried by a user; and a sensing unit within said housing con-figured to characterize an object located in proximity to the portable system, said sensing unit comprising: a wideband electromagnetic transducer array said array comprising a plurality of electromagnetic transducers; a transmitter unit for applying RF signals to said electromagnetic transducer array; and a receiver unit for receiving coupled RF signals from said electromagnetic transducers array.

20 Claims, 13 Drawing Sheets

Related U.S. Application Data continuation of application No. 16/174,599, filed on Oct. 30, 2018, now Pat. No. 10,321,843, which is a continuation of application No. 15/114,861, filed as application No. PCT/IL2015/050099 on Jan. 28, 2015, now Pat. No. 10,182,738.

(60) Provisional application No. 61/932,477, filed on Jan. 28, 2014.

(51) Int. Cl.
| | |
|---|---|
| *A61B 5/00* | (2006.01) |
| *G01S 13/89* | (2006.01) |
| *G01S 7/03* | (2006.01) |

(52) U.S. Cl.
CPC .......... *A61B 5/4312* (2013.01); *A61B 5/4872* (2013.01); *A61B 5/6898* (2013.01); *G01S 7/02* (2013.01); *G01S 7/032* (2013.01); *G01S 13/89* (2013.01); *A61B 2560/0431* (2013.01); *A61B 2562/0228* (2013.01); *A61B 2562/046* (2013.01)

(58) Field of Classification Search
CPC .......... A61B 5/6898; A61B 2560/0431; A61B 2562/0228; A61B 2562/046; G01S 7/02; G01S 7/032; G01S 13/89
USPC ....... 324/329–348, 323, 447, 425, 200, 206, 324/256–259, 600, 637, 639, 658, 500, 324/750.12, 76.11, 144; 343/788, 867, 343/728, 893, 894, 712
See application file for complete search history.

(56) References Cited

U.S. PATENT DOCUMENTS

| | | |
|---|---|---|
| 7,387,010 B2 | 6/2008 | Sunshine |
| 7,668,046 B2 | 2/2010 | Banker |
| 7,755,010 B2 | 7/2010 | Godshalk |
| 8,050,740 B2 | 11/2011 | Davis |
| 8,095,204 B2 | 1/2012 | Smith |
| 9,520,637 B2 | 12/2016 | Monte et al. |
| 10,182,738 B2 * | 1/2019 | Melamed ............. A61B 5/4312 |
| 10,321,843 B2 | 6/2019 | Melamed |
| 2003/0146767 A1 | 8/2003 | Steele |
| 2004/0077943 A1 | 4/2004 | Meaney |
| 2004/0190377 A1 | 9/2004 | Lewandowski |
| 2005/0040832 A1 | 2/2005 | Steele et al. |
| 2006/0176062 A1 | 8/2006 | Yang et al. |
| 2008/0036644 A1 | 2/2008 | Skultety-Betz et al. |
| 2010/0117885 A1 | 5/2010 | Holbrook et al. |
| 2011/0060215 A1 | 3/2011 | Tupin |
| 2012/0214412 A1 | 8/2012 | Schlub et al. |
| 2012/0242341 A1 | 9/2012 | Olsson |
| 2013/0231046 A1 | 9/2013 | Pope |
| 2013/0241780 A1 | 9/2013 | Amm |
| 2013/0300573 A1 * | 11/2013 | Brown ................. A61B 5/0002 340/870.01 |
| 2013/0329139 A1 | 12/2013 | Feher |
| 2014/0066757 A1 | 3/2014 | Chayat |
| 2016/0336643 A1 * | 11/2016 | Pascolini ............. H01Q 9/0421 |

OTHER PUBLICATIONS

European Communication t for corresponding EP15742707.1 dated Jun. 14, 2018.
European Communication t for corresponding EP15742707.1 dated Sep. 9, 2016.
European Search Report for corresponding EP20179505 dated Jul. 13, 2020.

* cited by examiner

SENSORS FOR A PORTABLE DEVICE

FIELD OF THE INVENTION

The present invention relates to microwave sensors and more specifically, but not exclusively, to microwave sensors for mobile devices and systems.

BACKGROUND INFORMATION

In recent years, the different types and the use of mobile devices has increased remarkably. If previously they included a limited group of telephones and laptop computers, it has now expanded to include, among others, smart phones, cellular phones, tablet devices, media players, portable gaming devices, digital cameras and laptop computers.

There are many causes to the proliferation of the use of these devices. One main reason is their size and weight. In the past, mobile devices were often heavy, large and/or cumbersome. Today, mobile devices manufactures compete with each other in how compact and lightweight they are.

Another reason is the relative ease and speed in which people can connect to the internet, which has become the new standard. Now people not only appreciate fast internet but need it and demand it. Even places with relatively poor infrastructure have maintained an ability to connect online via old and new technology, such as WiFi, WiMAX, LTE and others. Mobile devices make internet connectivity constantly accessible.

As mobile devices, such as smart phones and tablets become ubiquitous, the scope of their functions has broadened. People utilize their mobile devices for a plethora of actions and are constantly looking for more uses. For example, today, many mobile devices include extensive photographic systems, enabling, the user to take digital images and videos with cameras built into the device. These built-in cameras are often of high quality, with the ability to take photos and videos in color and with high resolution. These images can then be displayed, shared and modified, through various media.

With the growth of cloud storage capabilities and their easy access, mobile devices provide a practical tool for data accessibility. Furthermore, the advent and subsequent plenitude of applications for a wide spectrum of tasks, created specifically for use on mobile devices have further increased the dependence on these devices.

Mobile devices, while prolific and abundant as described above, have much potential to actualize. The medical profession and various other industries as well as the layman could benefit from further exploration of uses.

SUMMARY OF INVENTION

It is an object of the present invention to provide a sensor such as a microwave radar or a capacitive sensor configured to be attached or incorporated into a mobile or portable device.

It is yet another object of the present invention to provide a method and system that will allow obtaining information, for example but not limited to, testing of a drug to see if it has been tampered with, using a portable devise such as mobile phone or a tablet.

According to an aspect of some embodiments of the present invention there is provided a portable sensing system comprising: a portable device housing configured to be carried by a user; and a sensing unit within said housing configured to characterize an object located in proximity to the portable system, said sensing unit comprising: a wideband electromagnetic transducer array said array comprising a plurality of electromagnetic transducers; a transmitter unit for applying RF (radio-frequency) signals to said electromagnetic transducer array; and a receiver unit for receiving coupled RF signals from said electromagnetic transducers array.

In an embodiment said plurality of electromagnetic transducers are antennas.

In an embodiment said antennas are selected from a group consisting of: flat spiral antennas, printed log periodic antennas, sinuous antennas, patch antennas, multilayer antennas, waveguide antennas, dipole antennas, slot antennas, Vivaldi broadband antennas.

In an embodiment, said wideband electromagnetic transducer array is a MIMO (Multiple Input Multiple Output) antenna array.

In an embodiment, said plurality of electromagnetic transducers are capacitive sensor plates.

In an embodiment, said wideband electromagnetic transducer array is a capacitive sensor array.

In an embodiment, said capacitive sensor array comprises a plurality of feed lines and a plurality of receive lines wherein the plurality of feed lines are coupled to the receive lines through an electromagnetic field formed between at least two capacitive sensor plates said capacitive sensor plates connected to said feed and receive lines, wherein the capacitive sensor plates are configured to identify or quantitatively characterize the object.

In an embodiment, said object is located within the formed electromagnetic field.

In an embodiment, the sensor unit comprises a plurality of layers, wherein the feed lines are placed it separate layers and are connected to the sensing plates through vertical holes said holes interconnecting the layers and wherein a plurality ground layers are located between and around the layers.

In an embodiment, a sensing area is formed between two adjutant capacity plates.

In an embodiment, the capacitive sensor array is formed as a grid structure.

In an embodiment, the portable sensing system comprises a data acquisition unit for collecting and digitizing said coupled RF signals.

In an embodiment, the data acquisition unit is configured to tag the coupled RF signals according to the electromagnetic transducer array combination and the time at which the coupled RF signals were collected.

In an embodiment, the portable sensing system comprises a processing unit said processing unit is configured to convert the RF signals into a set of responses said responses characterizing the object, and convert the set of responses into data.

In an embodiment, said date is image data.

In an embodiment, said image date is a three dimensional image data said image data comprises an external and internal structure of the object.

In an embodiment, the data is displayed at said portable device display.

In an embodiment, the sensing unit is releasable from the portable system.

In an embodiment, the sensing unit is configured to scan the object.

In an embodiment, the sensing unit is movable with respect to the object.

In an embodiment, the sensing unit is linearly movable or rotationally movable with respect to the object.

In an embodiment, the object is movable with respect to the sensing unit.

In an embodiment, the portable device is a portable cellular telephone.

In an embodiment, the RF signals are selected from the group consisting of: pulse signals, stepped-frequency signals and chirp signals.

In an embodiment, said wideband electromagnetic transducer array comprises a layer of matching material for improved coupling of the electromagnetic transducers radiation to said object.

According to a second aspect of some embodiments of the present invention there is provided a portable sensing system, the system comprising: a portable device housing configured to be carried by a user; and a sensing unit within said housing configured to characterize an object located in proximity to the portable system, said sensing unit comprising: wideband antenna array unit said array unit comprising a plurality of antennas; a transmitter unit for generating a plurality of microwave signals to said antenna array; and a receiver unit for receiving reflected microwave signals from said antenna array unit.

In an embodiment, the portable sensing system comprising a capacitive sensor for characterizing the object, wherein said object is placed on said capacitive sensor surface.

In an embodiment, said capacitive sensor comprises a plurality of feed lines and a plurality of receive lines wherein the plurality of feed lines are coupled to the receive lines through an electromagnetic field formed between at least two capacitive sensor plates connected to said feed and receive lines to identify or quantitatively characterize the object wherein said object is located within the formed electromagnetic field.

According to a third aspect of some embodiments of the present invention there is provided a portable sensing device, the device comprising: a portable device housing configured to be attached to the portable device; and a sensing unit within said housing configured to scan and characterize an object located in proximity to the sensing unit, said sensing unit comprising: a wideband antenna array unit said array unit comprising a plurality of antennas; a capacitive sensor array; a transmitter unit for generating a plurality of microwave signals to said antenna array; and a receiver unit for receiving reflected microwave signals from said antenna array unit.

In an embodiment, the sensor unit is releasable from the portable device.

According to a third aspect of some embodiments of the present invention there is provided a method for providing microwave imaging functionality for a portable device, the method comprising: attaching to said portable device a housing, said housing comprising: a sensing unit said sensing unit comprises a wideband electromagnetic transducer array said array comprising a plurality of electromagnetic transducers; a transmitter unit for applying RF (radio-frequency) signals to said electromagnetic transducer array; and a receiver unit for receiving a plurality of coupled RF signals from said electromagnetic transducers array; a data acquisition unit; capturing microwave image data by said sensing unit; and transmitting the microwave image data to the portable device.

In an embodiment the method comprising presenting said image data at said portable device display.

According to a fourth aspect of some embodiments of the present invention, there is provided a portable sensing system comprising: a housing configured to be attached to a portable device and a sensing unit within the housing, the sensing unit is configured to provide microwave data of an object.

In an embodiment, said sensing module is a MIMO radar module.

In an embodiment, the MIMO radar module comprises a wideband antenna array connected to a transmitter/receiver unit, and said transmitter/receiver unit is configured to generate microwave signals to said antenna array.

In an embodiment, said antenna array comprises a plurality of receive antenna and transmit antennas.

In an embodiment, said antennas may be selected from a group consisting of: flat spiral antennas, printed log periodic antennas, sinuous antennas, patch antennas, multilayer antennas, slot antennas In an embodiment, said sensing system comprises capacitive sensor unit configured to characterize said object.

Prior to the detailed specification of the invention being set forth it may be helpful to set forth definitions of certain terms that will be used hereinafter.

The term "electromagnetic transducer" as used herein and through the specification and claims should be understood to encompass a unit or device which couples the electromagnetic energy to the surroundings of the transducer and may comprise, among other, both antennas and capacitive sensor such as capacitive sensor plates.

The term "Radio Frequency " as used herein and through the specification and claims should be understood to encompass microwave portion of the spectrums and above, such as millimeter-wave and sub-millimeter-wave radiation.

The term "couple" or "coupling" as used herein and through the specification and claims should be understood to encompass wave signals being reflected from a substance or an object such as an object under test, and the electric field coupled between capacitive sensor plates through the medium composing the object under test.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which.

DETAILED DESCRIPTION

Figure 1A:
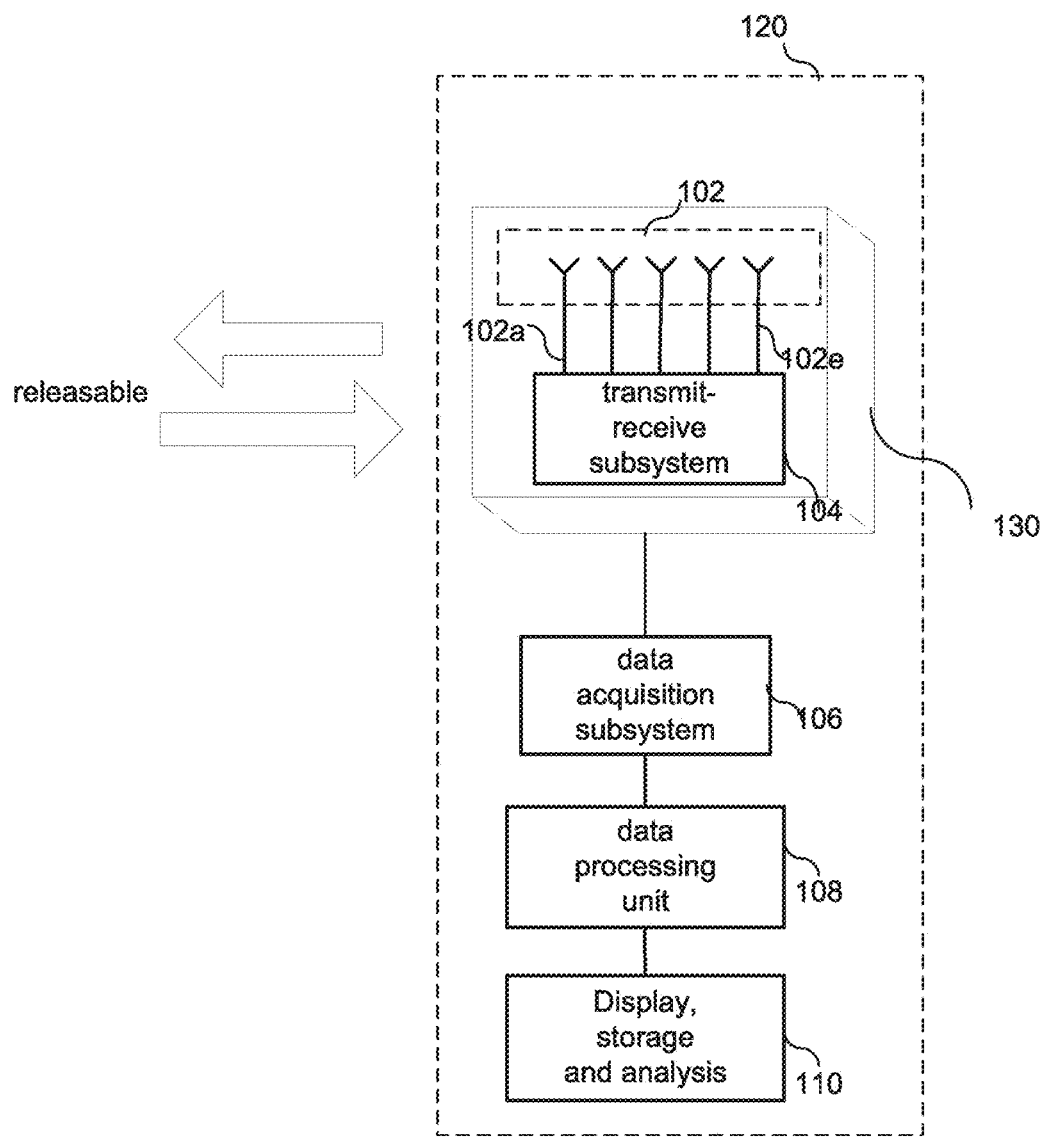
FIG. 1A is schematic view of a sensing system attached to or mounted on a mobile device, according to an embodiment of the invention.

The present invention relates to microwave or RF sensors and more specifically, but not exclusively, to microwave or RF sensors for portable devices. According to some embodiments of the invention a microwave sensor transmits microwaves towards a detection area and senses an object within that area through the reflection and modulation of the microwaves, for example by a Doppler effect from said object located in the detection area. Uses for this type of sensor range from motion-detection devices to biotechnology.

The present embodiments further provide a sensor system, device or unit that may be attached or incorporated into a portable device. According to one embodiment, the sensor system may include electromagnetic transducer such as a radar for microwave imaging and/or sensing of a medium or object under test (OUT). The radar may include an antenna array for enhanced imaging or sensing the OUT. According to another embodiment, the sensor system may include electromagnetic transducer in the form of one or more capacitive sensors or probes configured to sense and/or detect and/or image one or more materials existing within the OUT. According to another embodiment the sensor system may identify a body or substance approaching the sensor system and may alert or identify the type of the object approaching the sensor system. It is to be understood that both antennas and capacitive sensor fall within the scope of "electromagnetic transducer".

The sensor system may further include a transmitter unit and a receiver unit for applying and receiving accordingly RF (radio-frequency) signals or coupled RF signals to or from the electromagnetic transducer. The RF signals may be wideband or ultra-wideband signals.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Microwave Radar Imaging

Referring now to the drawings, FIG. 1 illustrates a sensing unit 130 configured to be attached or included in a device such as a portable device 120. According to some embodiments, the portable device 120 may be a handheld device or a handheld computer such as a mobile telephone, a smart phone, a tablet computing device, a laptop computing device, a personal digital assistant, a visible light camera, a personal video device or a music player, personal media player, global positioning system navigational device, pager, portable gaming device or any other appropriate mobile device known in the art. For example, the sensing unit 130 may be configured to capture, characterize, process, and/or identify, or define an object such as OUT and provide an identification results relating to the OUT to the portable device 120 for use in any desired fashion (e.g., for further processing, to store in memory, to display, to use by various applications running on the portable device 120, to export to other devices, or other uses).

In one embodiment, the sensor unit 130 may be a multi-layer structure implemented at least part with printed circuit board techniques using appropriate dielectric materials. Commonly used materials are glass-epoxy, Teflon-based materials. Layers of high-dielectric-constant materials can be incorporated in order to match the antennas to materials under test.

The sensing unit 130 may include or may be connected to a transmit/receive subsystem 104, a data acquisition subsystem 106, a data processing unit 108 and a console 110.

According to one embodiment of the invention, the sensing system 130 may include one or more antennas such as antenna array 102. For example the antenna array 102 may include multiple antennas 102a-102e typically between a few and several dozen (for example 30) antennas. The antennas can be of many types known in the art, such as printed antennas, waveguide antennas, dipole antennas or "Vivaldi" broadband antennas. The antenna array can be linear or two-dimensional, flat or conformal to the region of interest.

According to some embodiment of the invention the antenna array 102 may be an array of flat broadband antennae, for example spiral shaped antennae. The antenna array 102 may include a layer of matching material for improved coupling of the antenna radiation to the materials or objects under test. The unique and optimized shape of the antenna array, enables their use in limited sized mobile devices, such as a thin, small-sized smart phone or tablet. In addition, the use of an antenna array made as flat as possible, for example in a printed circuit, allows for the linkage of the sensing unit 130 to any mobile device known in the art, as it does not take up much space in the mobile device, it is not cumbersome, nor does it add significant weight to the portable device 120.

The transmit/receive subsystem 104 is responsible for generation of the microwave signals, coupling them to the antennas 102a-102e, reception of the microwave signals from the antennas and converting them into a form suitable for acquisition. The signals (e. g. RF signals) can be pulse signals, stepped-frequency signals, chirp signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates. The transmit/receive subsystem 104 can perform transmission and reception with multiple antennas at a time or select one transmit and one receive antenna at a time, according to a tradeoff between complexity and acquisition time.

The data acquisition subsystem 106 collects and digitizes the signals from the transmit/receive subsystem 104 while tagging the signals according to the antenna combination used and the time at which the signals were collected. The data acquisition subsystem will typically include analog-to-digital (A/D) converters and data buffers, but it may include additional functions such as signal averaging, correlation of waveforms with templates or converting signals between frequency and time domain.

The data processing unit 108 is responsible for converting the collected signals into a set of responses characterizing the OUT, and performing the algorithms for converting the sets of responses, for example into image data.

An example of algorithm for converting the sets of responses may be for example Delay and Sum (DAS) algorithm.

The DAS algorithm for reconstructing an image from impulse responses of the medium is well-known, and is used here as a reference. For each point r in some designated volume in the three dimensional space, and for each antenna element pair (from antenna element i to antenna element j) the expected delay $T_{ij}(r)$ from antenna element i to point r and back to antenna element j is calculated, considering the propagation velocity through the medium (which is assumed to have known electrical properties). Then the reconstructed image at location r is created by summing the estimated impulse responses of each pair i,j after shifting them by delay $T_{ij}(r)$, i.e.

$$s(r) = \Sigma_{ij} h_{ij}(T_{ij}(r)) \quad (1)$$

where the summation is over all antenna element pairs.

Assuming a reflector exists at point r then we expect a positive pulse to exist at position Tij(r) in all, or most, pairs, creating high intensity of the reconstructed image at this point.

DAS assumes the responses $h_{ij}(t)$ refer to the impulse response of the medium under test. However since the components involved in the measurement have responses varying in frequency and space, the direct measurement involves a combination of the medium response and the response of these components. The antenna elements used for transmission and reception proposes are usually of a high-pass nature, not being capable of transmitting very low frequencies. The frequency response of transmission/receive microwave circuits may exhibit variations due to production, aging, and temperature, and it is preferable to measure that response and take it into account.

Typical image reconstruction algorithms (such as DAS) assume perfect antenna elements, and therefore the above effects are compensated for before applying the reconstruction algorithm, e.g. by dividing the frequency response obtained from the measurement by the known frequency response of the components. As mentioned previously, this pre-calibration compensation is sub-optimal as it amplifies noise, and does not take into account that some antenna elements at some frequencies see a target better than others, nor does it apply to location-dependent amplitude and phase shift variations.

Examples for such algorithms may be found in US Patent Application Publication No. US20140066757, entitled "WIDEBAND RADAR WITH HETEROGENEOUS ANTENNA ARRAYS" which application is incorporated by reference herein in its entirety.

According to one context of the invention described herein, unit 108 is responsible for Doppler processing as well, in which changes in the response over time are taken into account along with the response itself. The data processing unit is usually implemented as a high-performance computing platform, based either on dedicated Digital Signal Processing (DSP) units, general purpose CPUs, or, according to newer trends, Graphical Processing Units (GPU). In some embodiments, the acquisition unit and/or processing unit may be connected to other sensors and integrate the data from those sensors to construct the images, as will be further shown in FIGS. 3-5.

A final step in the process is making use of the resulting image, either in the form of visualization, display, storage, archiving, or input to feature detection algorithms. This step is exemplified in FIG. 1A as console 110. The console in a mobile device is typically implemented as a handheld computer such as a mobile telephone or a table computer with appropriate application software.

According to system type, the computer can be stationary, laptop, tablet, palm or industrial ruggedized. It should be understood that while FIG. 1A illustrates functional decomposition into processing stages, some of those can be implemented on the same hardware (such as a common processing unit) or distributed over multiple (such as graphical processing unit, GPU) and even remote pieces of hardware (such as in the case of multiprocessing or cloud computing).

According to one embodiment of the invention, subsystems 106, 108 and 110 may be part of the sensing unit or the portable device 120, as shown in FIG. 1A. Alternatively the sensing unit 130 may be included within a housing 125 such as case or a jacket configured to be releasable (i.e. connected or disconnected) to the portable device 120. For example the sensing system 130 may include the antenna array unit 102 and the transmit/receive-subsystem 130 may be part of the housing 125 which is electrically or wirelessly connected to the portable device 120, for example through a dedicated connection such a USB connection, wireless connection or any connection known in the art.

Following the connection of the sensor unit 130 to the portable device, the sensor unit 130 may utilize the portable device's own data acquisition, data processing display, storage and analysis subsystems.

Capacitive Sensor

Figure 1B:
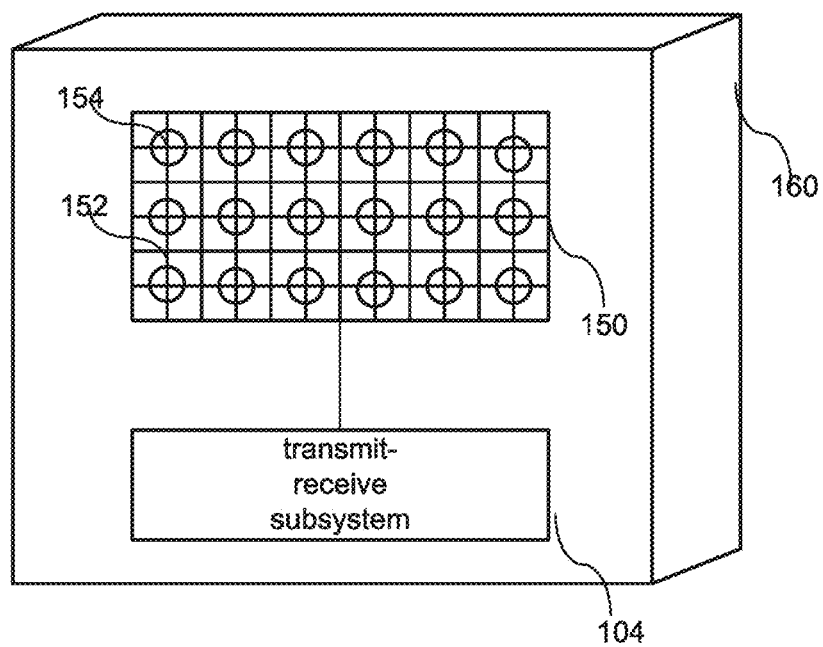
FIG. 1B depicts the sensing system including a capacitive sensor, according to an embodiment of the invention.

According to one embodiment as shown in FIG. 1B a sensor system 160 may include a capacitive sensor such as an array capacitive sensor 150 configured to sense an OUT located in proximity or on the sensing system surface. For example, the OUT may be liquid or ointment and the sensor system 150 may identify the components (e.g. the type and amount) found within a drop/particle of the liquid or ointment sprayed for example by a portable device user on the sensor system 160 incorporated in his personal portable device. The results identified by the sensor system 160 may be further displayed on the user's portable device display.

According to one embodiment the capacitive array sensor 150 may include a number of sensing lines such as feed lines 154 which may be organized in a structure of, but not limited to a grid. Additionally, the array sensor 150 may include a plurality of sensing plates at the surface of the sensor, connected to the feed lines 154. Each of the feed lines is coupled to one or more corresponding receive lines through an electromagnetic field formed between at least two plates connected to said lines, to identify and/or quantitatively characterize an object located within the formed electromagnetic field. In one embodiment, the sensor 150 may include a number of layers, where the feed lines 152, such as the column and row feed lines are placed in separate layers, and are connected to the sensing plates through vertical metalized holes (e.g. vias) interconnecting the layers. In some embodiments, a plurality of ground layers are located between and around the layers thus separating (e.g. screening) the row feed lines, the column fed lines, the sensing plates, and possibly the back-side of the capacitive array sensor 150, from each other. A detailed description of sensor 150 is illustrated in FIG. 2.

Figure 1C:
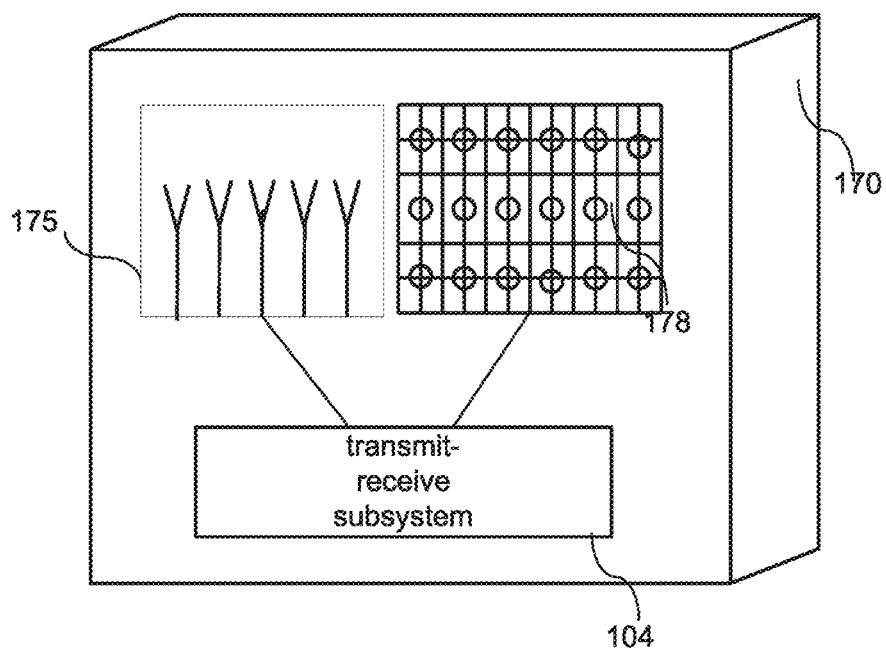
FIG. 1C depicts the sensing system including a microwave sensor and capacitive sensor, according to an embodiment of the invention.

As shown in FIG. 1B the capacitive array sensor 150 may be connected to the transmit/receive subsystem 104 for generation of signals to the capacitive sensors FIG. 1C illustrates a sensor system 170 comprising two types of sensors: an antenna array sensor 175 configured to identify OUT located remotely from the sensor module 170 and a capacitive sensor 178 configured to identify OUT located in proximity or at the near-field of the sensor system.

Figure 2:
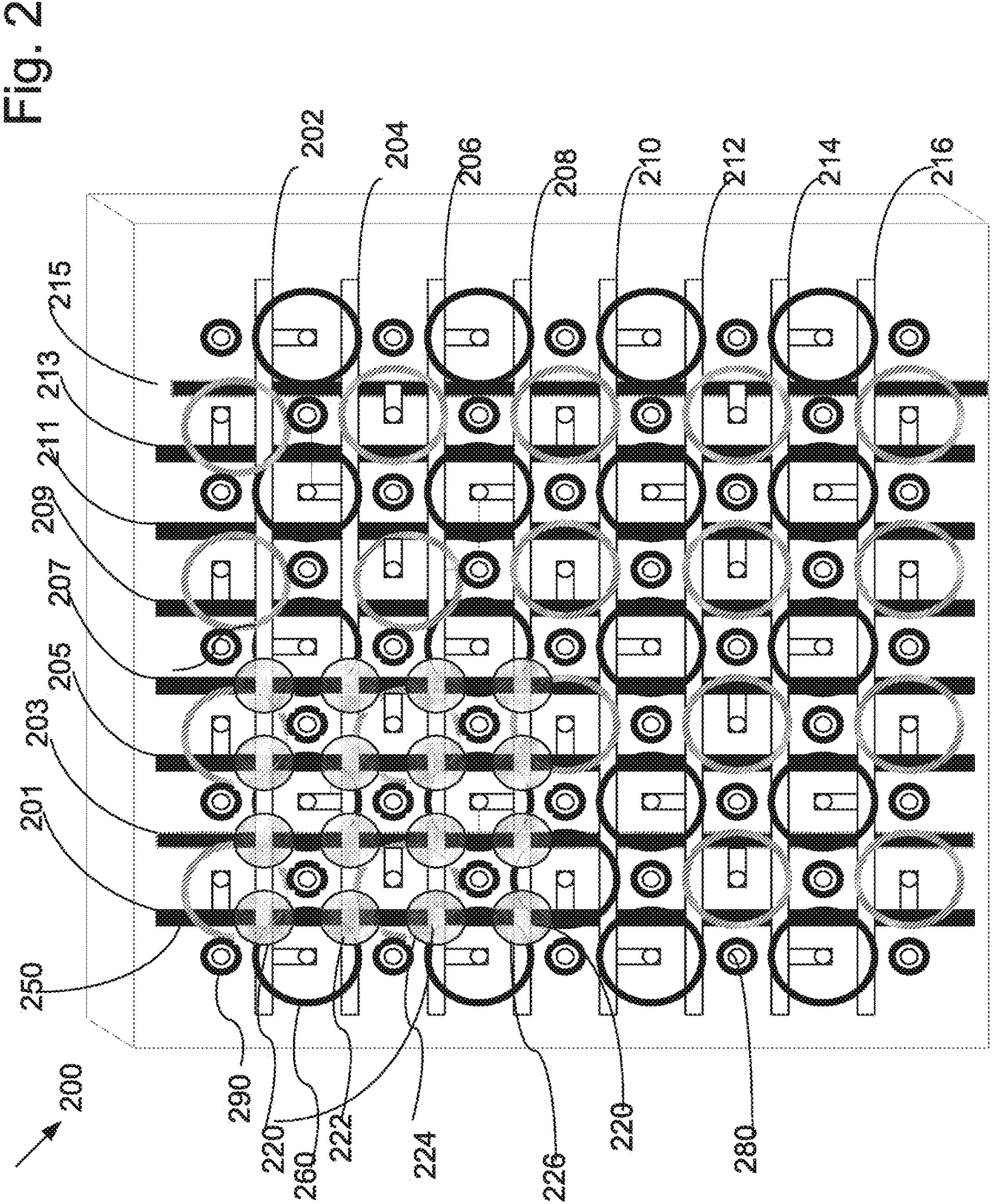
FIG. 2 is a depiction of the of the sensing system topology, according to an embodiment of the invention.

Reference is now made to FIG. 2 which illustrates an exemplary topology of a sensing system 200 including a plurality of capacitive sensors according to one embodiment of the invention. The sensing system 200 may be implemented, for one or more embodiments, with a small form factor and in accordance with wafer level packaging techniques or other packaging techniques, for example. The sensing system 200 may be a multi-layer structure implemented at least in part using a material such a glass-epoxy or a Teflon based PCB material.

Definitions:
White lines 202-216: are row feed lines/boards (e.g. "layer 1");
Black lines/boards/boards 201-215: are column feed lines/boards (e.g. "layer 2");
Black circles and gray circles/rings: are row/column sensing plates, typically located at the top layer of the sensing system 200;
Small white circles 280 are vias interconnecting the layers;
Black circles 290 indicate vias interconnecting all the ground planes;
Gray circles 220 indicate the "sensing as areas" created by corresponding pairs of row/column excitation/sensing;

In one embodiment, the sensing system 200 may be a PCB 201 (Printed Circuit Board) including a plurality of layers, for example 6 layers. In "layer 1" the PCB 201 includes a plurality of "excitation" feed lines 202-216 which are orthogonal to a plurality of "sensing" feed lines 202-216 located for example in the PCB 201 "layer 2". Feed lines 202-216 may be activated by a touch of an object and may further activate/excite "sensing" feed lines 201-215 (i.e. the green lines are stimulated and the red lines are sensed). For example feed lines 202-216 and lines 201-215 may include, respectively, a plurality of sensing plates 250 and 260 located at the PCB 201 top layer and are configured to sense an object located in their proximity or in contact with them.

As shown in FIG. 2, the sensitive areas between the sensing plates 250 and 260 are marked in circles 220. Circles 220 indicate the "sensing areas" created by corresponding pairs of row/column feed lines 202-216 and 201-215. For example, if one were to place an object between two sensing plates, for example between plates 201 and 204, the passageway between them, situated in circle 222, will be affected by the material.

For example the dripping of a drop of a material on PCB 201 in a particular area of the sensing system, for example in circle 222, will affect the capacitance level between the two neighboring 'sensing plates'. A change in the size of the passage between two sensing plates relates to the attachment capacitance between the two sensing plates (e.g those drawn in black and those drawn in gray, for example 250 and 260). A passageway between each pair of sensing plates is affected by the material found between them. This means that the area close to their overlapping region (they are not actually overlapping as there is a space between them) will affect their electromagnetic capacitive coupling. The uniqueness of the topology presented in FIG. 2 is that it, enables to quantitatively characterize, specifically with "high resolution", an object placed on the PCB 201 by each of the indicated areas which marked by circles 222 via stimulating a particular red element and receiving through a particular green element.

The main advantages of the sensing system 200 illustrated in FIG. 2 are as follows:

A. The elements (e.g. capacitive sensing plates) in each row and in each column have separate feed lines for the odd numbered and even numbered elements, allowing double the resolution compared to the case in which all the elements in a row are connected together. In other words, while according to prior art topology a system including for example N*N sensors, will not provide $N^2$ measurements, but rather $2N^2$ measurements since there is no separation between the sensing areas (as all the sensors are connected to the same feed line), according to the present invention topology, each "sensing plate" is independent, allowing each capacitive sensor to sense autonomously an object located in its proximity.

B. The capacitive sensor is formed in a grid structure where a single feed line (i.e. feed lines 202) may simultaneously excite a plurality of feed lines (i.e. feed lines 201-215).

C. The "high resolution measurement topology" presented hereinabove, allows for quantitative measurements with high resolution using a relatively small sized PCB. For example the PCB may be 10×10 mm to 30×30 mm size.

D. The screening of respective lines, enables an accurate "high resolution" quantitative sensing of dielectric properties versus location. In other words, according to prior art solution information relating to an object placed on a sensor relates only to specific sensing zones e.g. the location of a drop of water placed on a sensor could be located, but not details of the water itself (i.e. is it salty or not).

Portable Device Sensing Methods

Figure 3A:
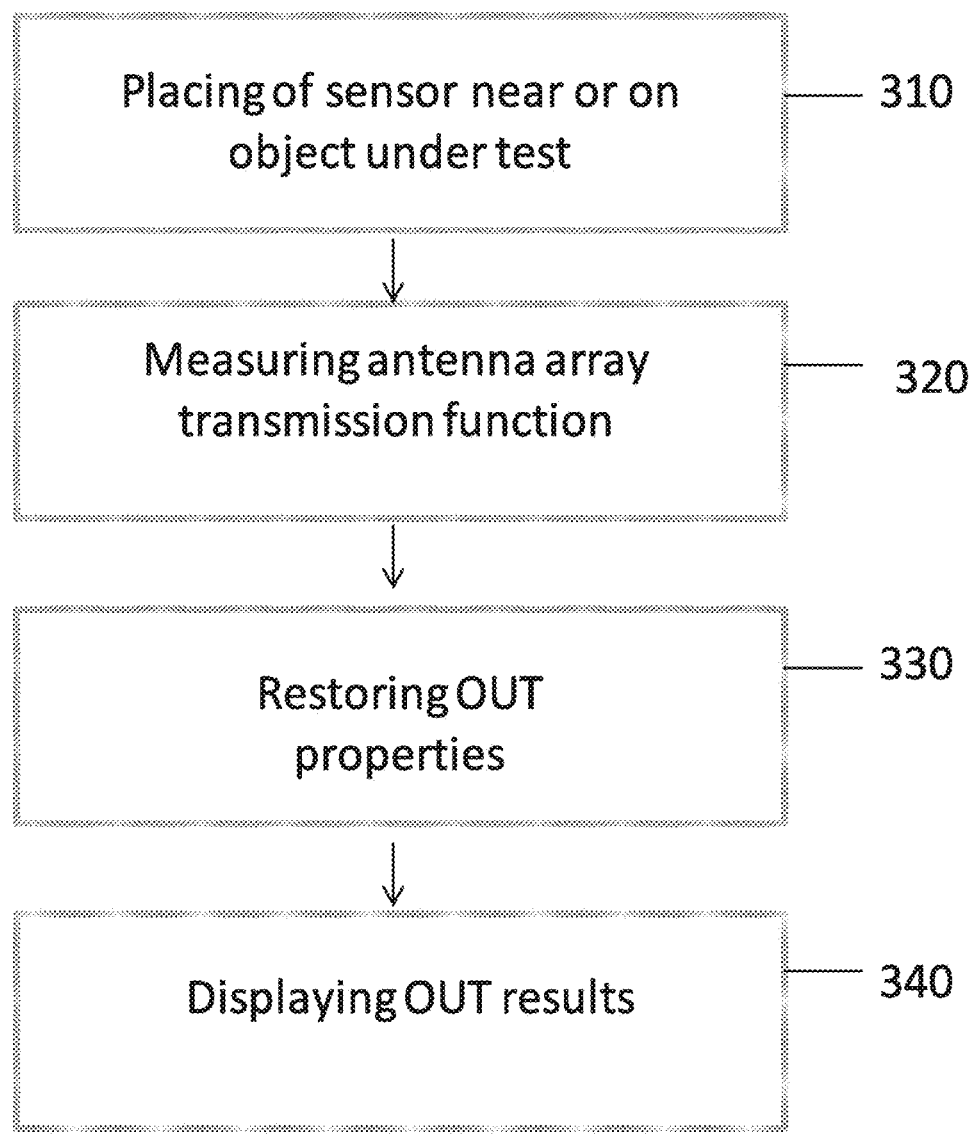
FIG. 3A is a flow chart showing the process of identifying a material via a portable device sensing system, according to an embodiment of the invention.

Reference is now made to FIG. 3A, which is a flow chart showing a process of identifying an OUT via a portable device sensing system. Step 310 includes attaching a sensor system or unit, such as sensor system 150 or 160 shown in FIGS. 1A and 1B placed for example on the back of a mobile device, to the OUT, to characterize the OUT inside. For example the portable device 130 may be attached to a vegetable or a fruit to characterize identify and locate an organic material found inside the vegetables or fruit.

Figure 3B:
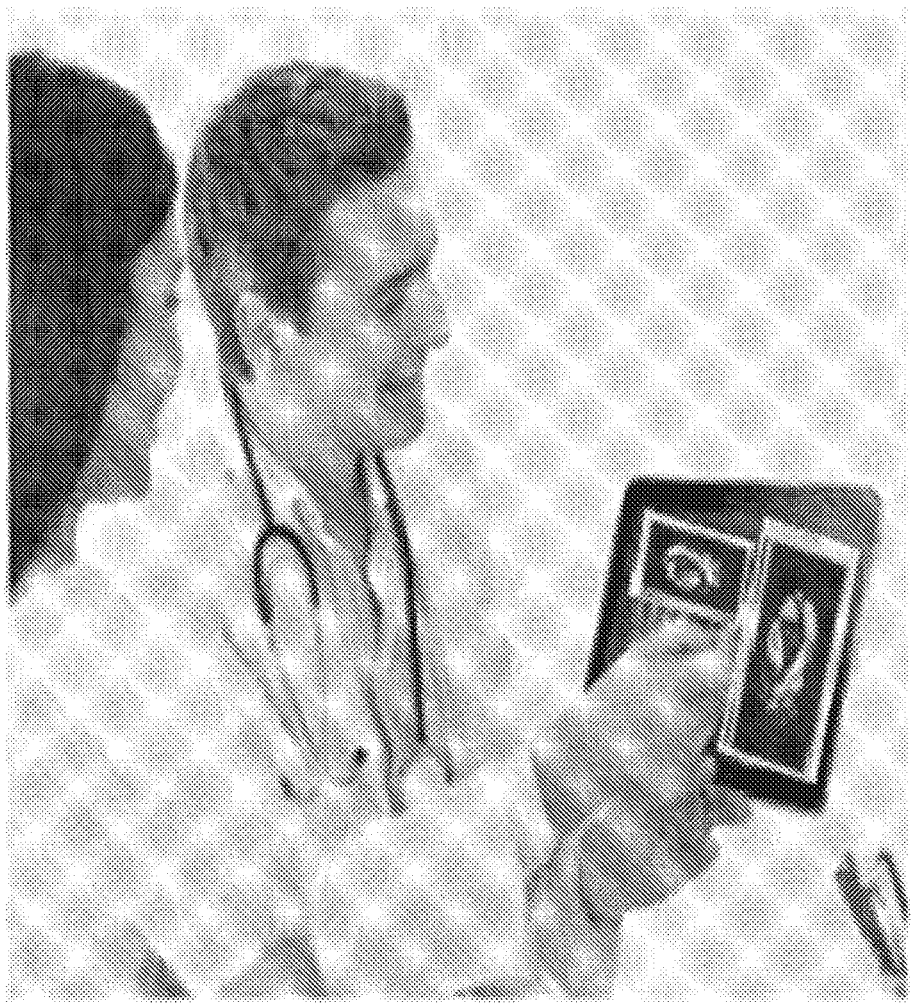
FIGS. 3B-3C show a number of exemplary uses of the microwave sensor mounted on the mobile device, according to some embodiments of the invention.
Figure 3C:
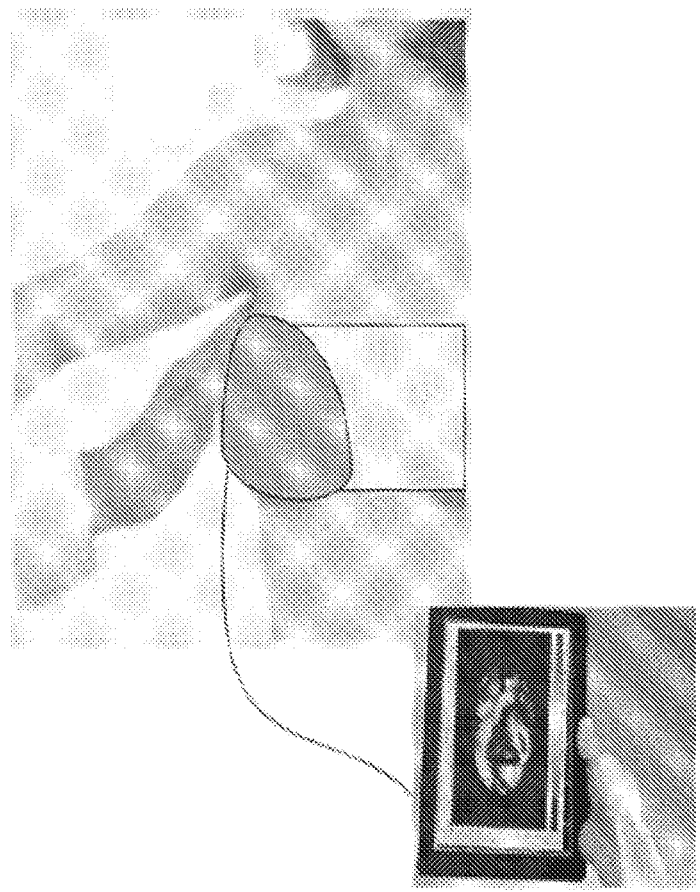

Step 320 includes measuring the antenna array "transmission function" which includes measuring various combinations of transmitting and receiving antennas. For example the "transmission function" process is carried out by intermittently transmitting a signal from one antenna and receiving a signal by one or more of the antennas in order to characterize the OUT located in front of the antenna array. Step 330 includes restoring the properties of the OUT, based on the OUT returns signals and step 340 includes displaying the OUT structure, for example on the screen of a mobile device as shown. For example, FIGS. 3B and 3C illustrate application of a MIMO (Multiple Input Multiple Output) radar system incorporated in a tablet for the examination of a woman's breast. In this illustration, the antenna array 102 is coupled to the breast. The antennas 102a-102e of the array 102 are situated in a conformal cup-like shape. The purpose of the MIMO radar system in such application is typically to search for malignant tumors.

According to some embodiments of the invention, the sensor system, such as sensor system 150 or 160 shown in FIGS. 1A and 1B are configured to scan (e.g. scan may be defined as relative motion between the sensor and the DUT for example the sensing unit may be movable with respect to the object or sensing unit is linearly movable or rotationally movable with respect to the object or the object is movable with respect to the sensing unit) a DUT and provide a detailed image of the DUT such as a 3D (three dimensional) image (e.g. providing a physical measurements of the DUT onto a computer in an organized manner). The image may include the external and internal structure of the DUT such as its void and/or wall thickness. For example the DUT may be a cup or a human organ or any tangible object and a user may scan the DUT placed in proximity to his mobile devise. The user may surround the DUT and scan the DUT from multiple angles, for example the DUT may be placed on a rotating stage and the user may scan the object from multiple angles, alternatively the user may simply move his mobile device sensors and surround the DUT. In the case of a flat object, such as a wall, the mobile device sensor can be moved along the wall in order to scan a larger area. The image may be displayed on the mobile device display and may be further printed or manufactured using manufacturing techniques known in the art such as 3D printing.

As illustrated in FIGS. 1B and 2, the mobile device may further include, one or more capacitive sensors configured to characterize the inside of an OUT. For example, to identify a material, such as the ingredients of a drug in real-time to see if the drug is real or fake, a capacitive sensors may be used to expose and characterize quantitatively the properties of the material, i.e. the properties of the drug. The capacitive sensors (as described in detail in FIG. 2), in contrast to the use of the sensory antennae, do not identify objects from a distance, rather it includes a number of sensing feed lines, whose purpose is to create an electromagnetic field toward the nearby lines, and via the use of the sensing lines, to characterise the material attached to the lines. For example, drug ingredients may be identified by dripping a drop from the drug on the sensor array surface.

Figure 4:
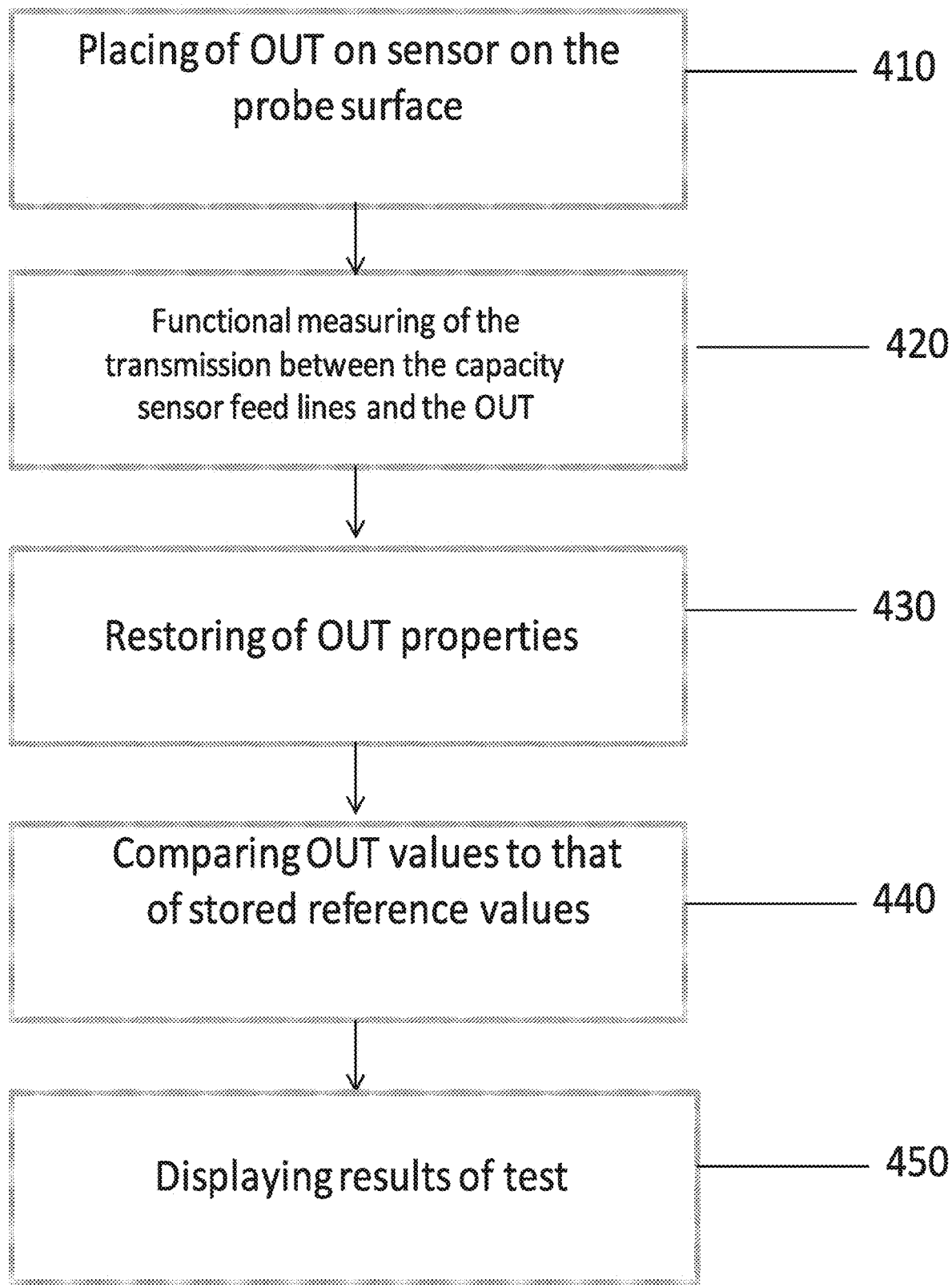
FIG. 4 is a flow chart showing the process of identifying quantitative qualities of an object, through the use of capacitive sensors attached to a mobile device, according to an embodiment of the invention.

FIG. 4 is a flow chart showing the process of identifying quantitative qualities of an OUT, through the use of capacitive sensors incorporated or attached to a portable device.

The identifying process begins in step 410, which includes attaching of placing the OUT on the sensor. For example, this step can be done through the sprinkling of a drop of the OUT on either a sensor's probe surface or on electrode surface, which are located for example on the back of a portable device. Step 420 includes reading the electromagnetic transmission function of the sensor's feed lines (i.e. functional measurement of the transmission between the capacitive sensor feed lines and the OUT) and step 430 includes restoring the OUT properties. Step 440, includes comparison the receive results in step 430 to the expected values from a reference material. For example, a user can download from the internet or via values provided by a pharmaceutical company on a 'cloud' to find out the expected values of the standard drug. Later on, the processing unit, for example of the mobile device or the external unit communicating with the mobile device will compare them to the results found in the test. Alternatively, the standard material's data can be saved in a storage compartment in the mobile device.

In step 450 the results of the test are displayed, for example if the drug is real or fake. Alternatively or additionally, one can display the results or the deviations on a screen. For example, the user can display that in a particular drug or material, abnormal components of a particular substance were found.

As stated in the flowcharts, one use of the sensors has been described regarding sensors mounted on a mobile device. The present invention includes many other uses and diverse applications of the mobile sensors which are described below.

Figure 5:
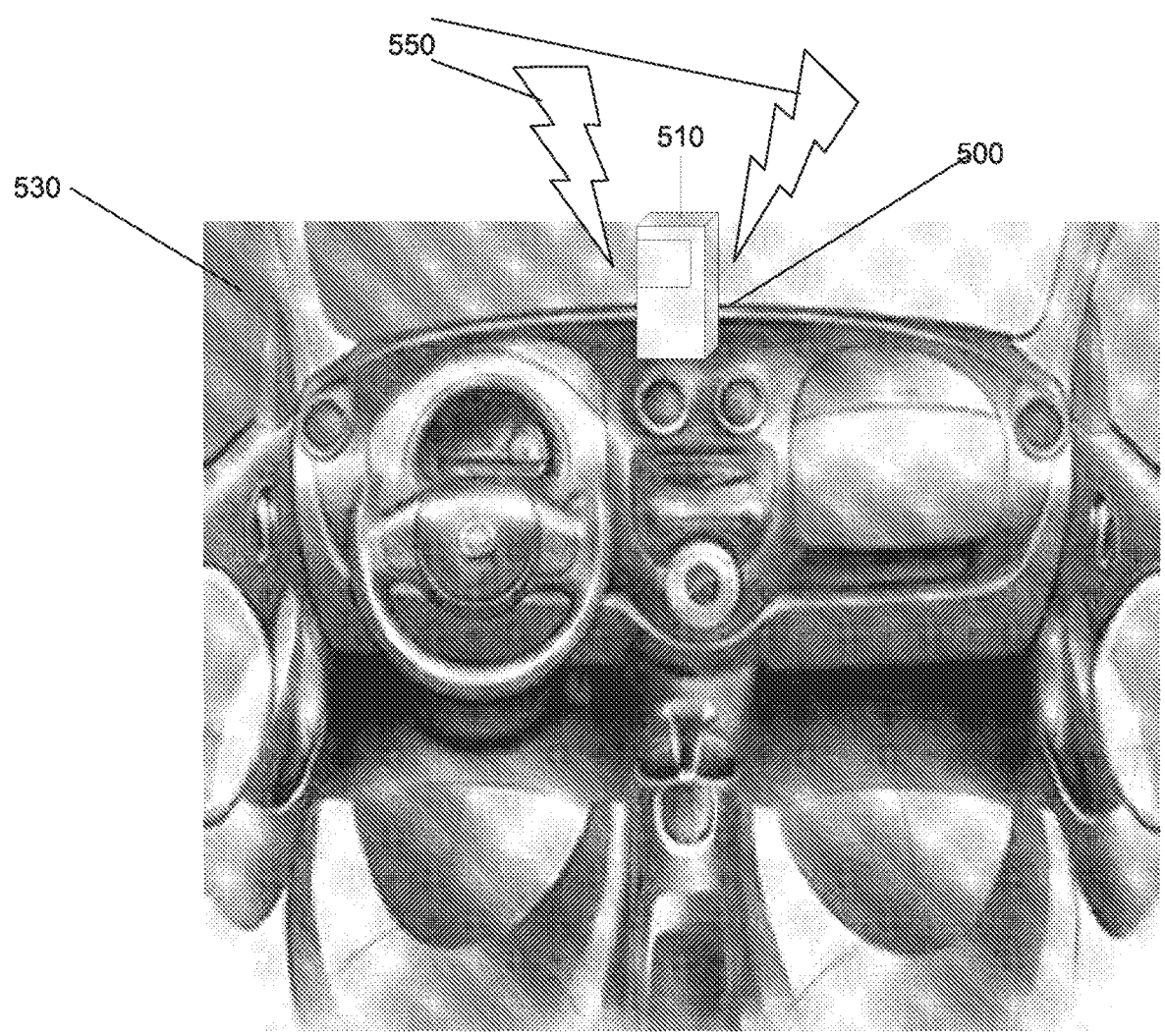
FIGS. 5-8 illustrate a number of exemplary uses of the microwave sensor mounted on the mobile device, according to other embodiments of the invention.

FIG. 5 describes use of a mobile device including the sensor system, for example as described in FIG. 1A, to be used as a warning signalling device for a vehicle that is too close, in prevention of traffic accidents.

For example, as described in FIG. 5, a mobile device user may install his mobile device 500 like a cellular phone on a car's dashboard. The mobile device may include sensory unit 510 airing RF 550 which can characterize and identify bodies approaching the vehicle. For example, if a vehicle is approaching closer than a specified distance defined in advance, a warning will appear on the display of the device. In addition, the mobile device could be attached to the vehicle, and automatically lower the speed until the car brakes, at the instant it senses immediate danger.

Figure 6:
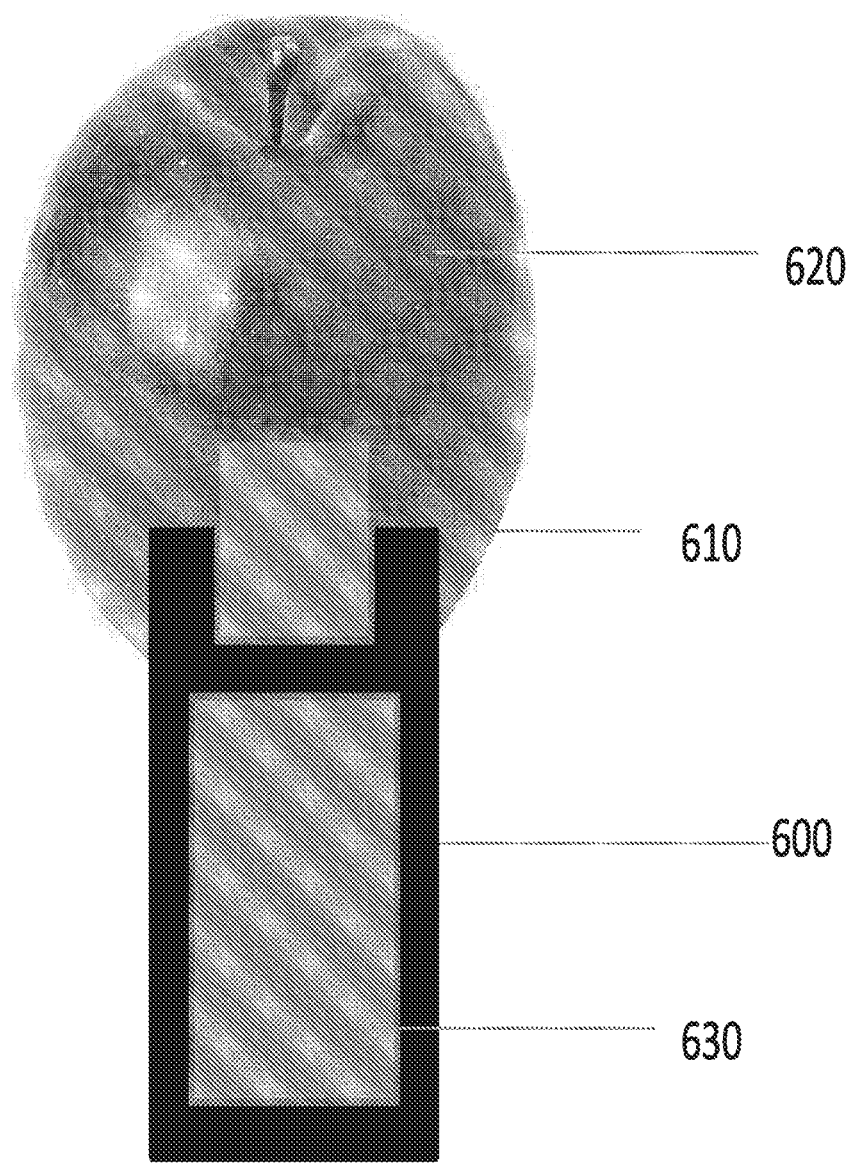

FIG. 6 describes the use of a mobile device including a sensing unit such as sensing system 150 illustrated in FIG. 1B to test if fruits and vegetables have pesticides on them. For example, one can place the device 600 on produce 620 so that the surface of the sensing system 610 is touching it directly. As described in FIG. 4, the functional reading of the electromagnetic transmission between the sensor's lines/boards and on produce 620. This reading is then compared to reference data and the results displayed, for example on the mobile device's monitor 630.

Figure 7:
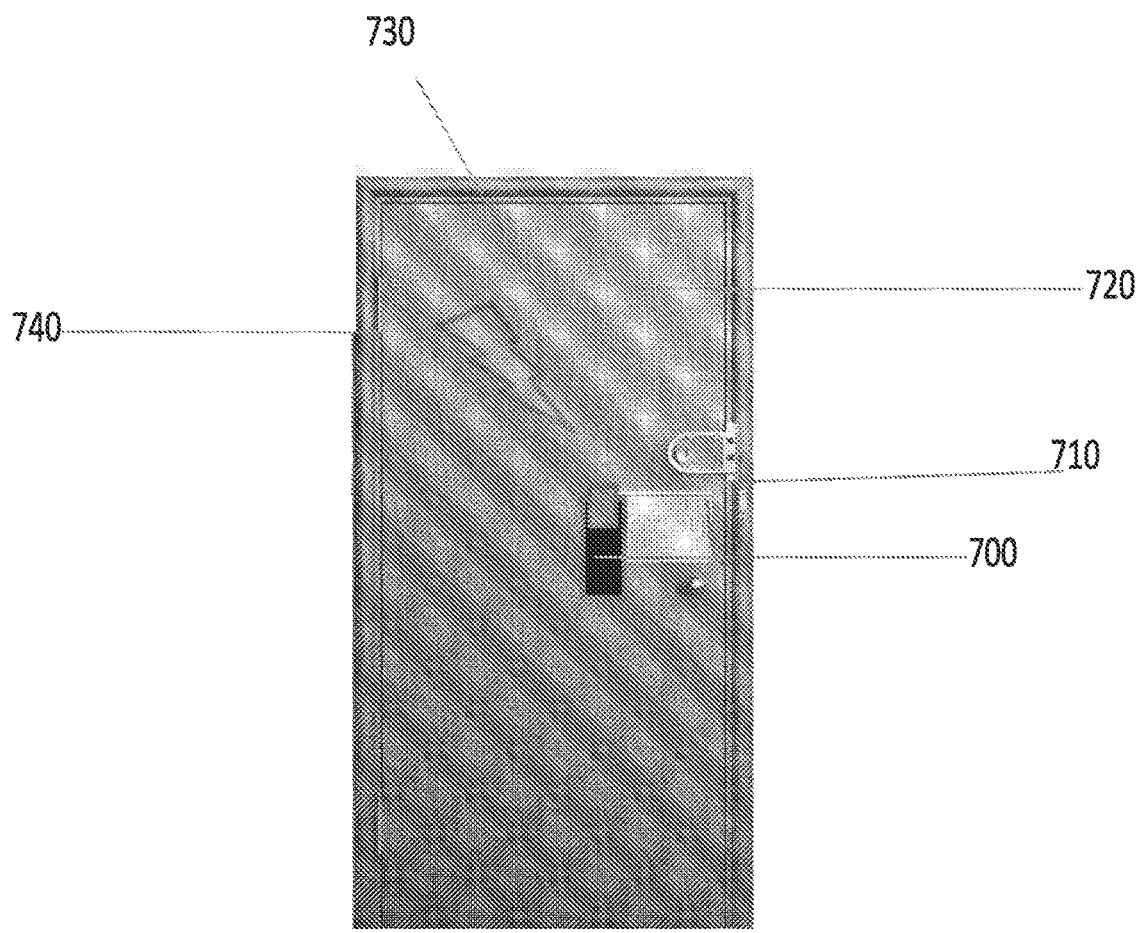

FIG. 7 describes the use of a mobile device including a sensing unit such as sensing system 130 illustrated in FIG. 1A to act as an alarm to be mounted on the front door 720 of a house or other place of residence. One can install a mobile device 700 on the door. This mobile device may include sensor unit 710 airing radio waves 740 which can characterize and identify bodies 730 approaching the door.

Figure 8:
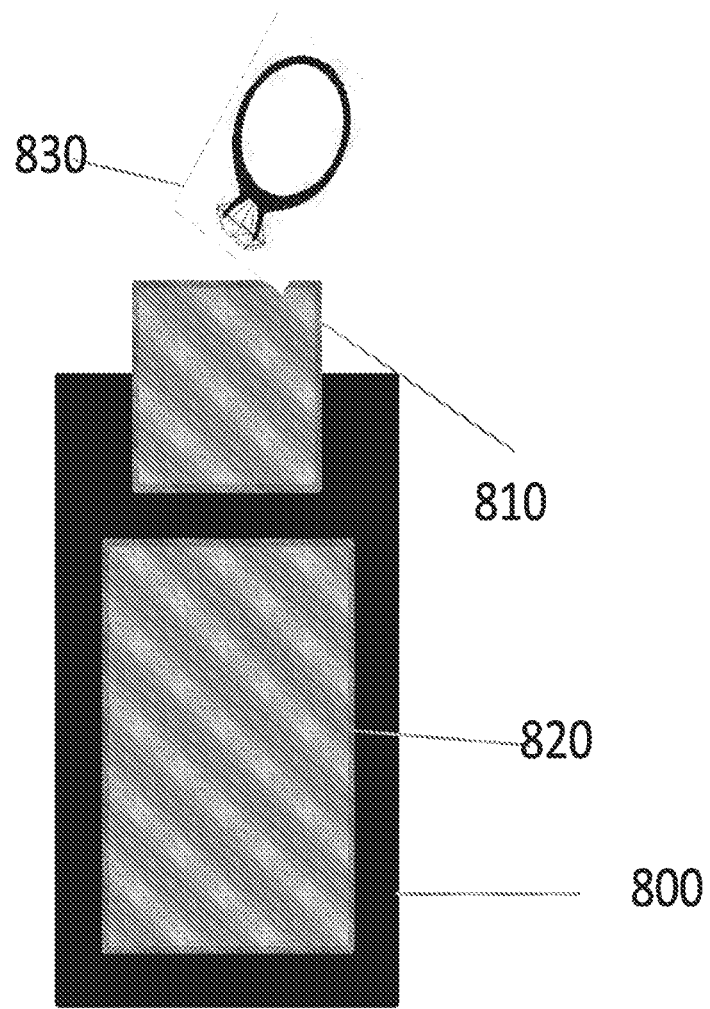

FIG. 8 depicts the use of a mobile device including the sensing system 130, to test whether an article of jewellery is fake or real. For example, once can place the device 800 near the jewellery 830 so that the sensing system 810 can read out the properties of the jewellery. After comparing the properties to a reference, a result is displayed on the screen 820.

Figure 9:
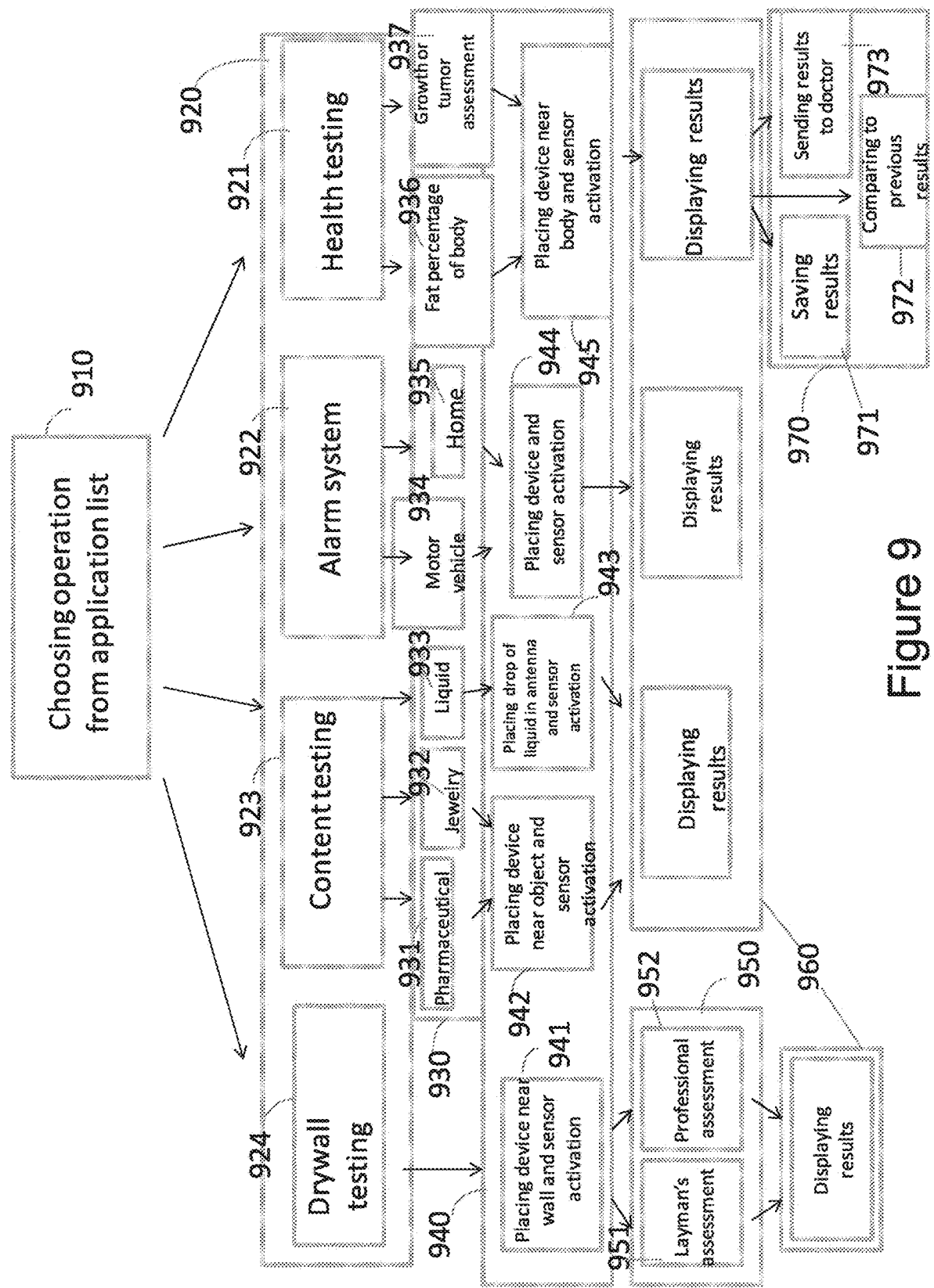
FIG. 9, is a flow chart that shows the steps of an object sensing procedure carried out by a mobile device, according to some embodiments of the invention.

Reference is now made to FIG. 9, which is a simplified flow chart that shows steps of an object sensing procedure carried out by a mobile device comprising a microwave radar and/or a capacitive sensor and modified to make provide images or sensing result of the object. The steps identified in FIG. 9 (and the order thereof) are exemplary and may include various alternatives, equivalents, or derivations thereof including but not limited to the order of execution of the same. The steps of the method of FIG. 9 (and its various alternatives) may be embodied in hardware or software including a non-transitory computer-readable storage medium (e.g., an optical disc or memory card) having instructions executable by a processor of a computing device. A user may launch or activate the method of FIG. 9 by opening or activating an application in a computing device such as a mobile device.

At step 910 a user, such as a mobile phone user, selects a purpose for using the sensor or a desired object need to be identified. The user may select an option from a list of categories listed in box 920 such as, but not limited to, health testing 921, alarm testing 922, content testing 923 or drywall testing 924. At the next step 930, the user may select a more specific option according to a sub-category. For example, the alarm system category 922, may have subcategories for various types of alarms such as but not limited to motor vehicle 934 or home 935, or the health testing category 921, may have subcategories for various types of health tests such as but not limited to fat percentage 936 or growth or tumour assessment 937.

In step 940 once the user selects the category and/or sub-category, he will be asked to place the mobile device or the object accordingly and then activate it. For example, when testing what is behind a drywall 924, after making his selection and being prompted, the user will place the mobile device 941 near the wall. When used as a car alarm 934, the user will place the mobile device on the dashboard 944. To test a liquid 933, the user will place a drop on the sensor. In one embodiment of the invention the user may activate the sensor through pressing a button on the mobile device after placement of the device close to or on the object to be tested.

After activation of the sensor, the test requested by the user is performed. The correct sensor will be implicated based on the test selection. For example, for a pharmaceutical drug testing 931, a capacitive sensor, such as capacitive sensor 170 shown in FIG. 1C will be used, whereas if testing what is behind a drywall 924, the microwave radar, such as radar 175 will be used.

In one embodiment of the invention the user can decide on the assessment type, in step 950, for example whether or not he or she wishes a professional 952 or layman's 951 assessment of the test, for example when testing what is behind a drywall.

Figure 10:
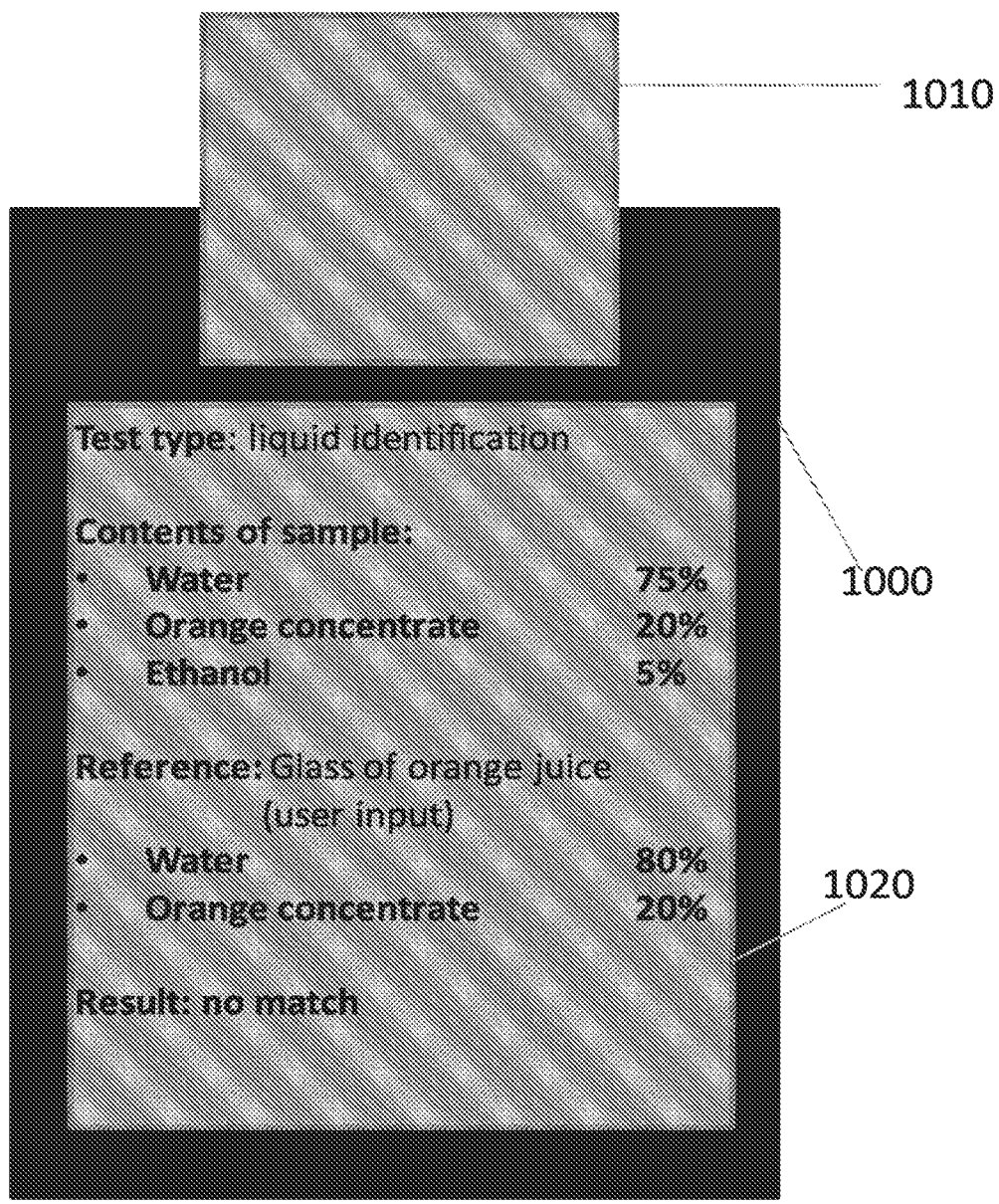
FIG. 10 illustrate an exemplary sensing results of an object displayed on a portable device screen, according to some embodiments of the invention.

In step 960, the results are displayed on the mobile device's interface, for example but not limited to a mobile device's screen, as depicted in FIG. 10. In one embodiment of the invention, in step 970 the user decides what to do with the results. In one embodiment of the invention, the user has the option of sending the results to his or her doctor 973. In another embodiment of the invention, the user has the option of saving the results 971, for example but not limited to a cloud. In another embodiment of the invention, the user has the option of comparing the results to previous results or other references 972, for example when using to test body fat percentage or a stored reference to compare standards of a drug.

In FIG. 10 the mobile device's interface is depicted. The mobile device 1000 is comprised of the device itself, the sensor 1010 and the interface 1020 on which the output of the results is displayed. The example in FIG. 10 demonstrates a possible result while performing a liquid identification test 933.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A portable device comprising:
   a portable device housing configured to be carried by a user; and
   a sensing unit within said housing configured to characterize an object, said sensing unit comprising:
      an antenna array sensor comprising a plurality of electromagnetic antennas and a capacitive sensor;
      a transmitter unit for applying RF (radio-frequency) signals to said plurality of electromagnetic antennas and to said capacitive sensor; and
      a receiver unit for receiving RF signals from said plurality of electromagnetic antennas and from said capacitive sensor;
   a user input via which the user selects one or more application categories for which the portable device is to be used; and
   at least one processor, wherein the at least one processor is configured to:

activate one or both of said electromagnetic antennas and said capacitive sensor according to the selected one or more application categories;

convert the RF signals into a set of responses said responses are configured to characterize the object; and convert the set of responses into data.

2. The portable sensing device according to claim 1, wherein the one or more application categories comprise contact and noncontact application categories.

3. The portable sensing device according to claim 2, wherein the antenna array sensor is configured to be activated upon said noncontact application category selection.

4. The portable sensing device according to claim 2, wherein the capacitive sensor is configured to be activated upon said contact application category selection.

5. The portable sensing device according to claim 2 wherein the processor is configured to process both said contact and noncontact application categories.

6. The portable sensing device according to claim 5 wherein said contact and noncontact application categories are selected from the group consisting of:
health testing; alarm testing; content testing; drywall testing.

7. The portable sensing device according to claim 1, wherein said plurality of electromagnetic antennas are selected from a group consisting of: flat spiral antennas, printed log periodic antennas, sinuous antennas, patch antennas, multilayer antennas, waveguide antennas, dipole antennas, slot antennas, Vivaldi broadband antennas.

8. The portable device according to claim 1, wherein said object is located within a formed electromagnetic field.

9. The portable device according to claim 1, wherein the capacitive sensor is formed as a grid structure.

10. The portable device according to claim 1, comprising a data acquisition unit for collecting and digitizing said RF signals.

11. The portable device according to claim 10, wherein the data acquisition unit is configured to tag the RF signals according to the plurality of electromagnetic antennas combination and the time at which the RF signals were collected.

12. The portable device according to claim 1, wherein said data is image data.

13. The portable device according to claim 12, wherein said image data is three dimensional image data.

14. The portable device according to claim 13 wherein said three dimensional image data comprises an external and internal structure of the object.

15. The portable device according to claim 1, wherein the data is displayed at said portable device display.

16. The portable sensing device according to claim 1, wherein the sensing unit is releasable from the portable device.

17. The portable sensing device according to claim 1, wherein the sensing unit is configured to scan the object.

18. The portable device according to claim 1, wherein the sensing unit is movable with respect to the object.

19. The portable device according to claim 1, wherein the portable device is a portable cellular telephone.

20. The portable device according to claim 1, wherein the RF signals are selected from the group consisting of pulse signals, stepped-frequency signals and chirp signals.

* * * * *